United States Patent
Murase et al.

(10) Patent No.: US 9,957,542 B2
(45) Date of Patent: May 1, 2018

(54) BIOSENSOR

(71) Applicant: CCI Corporation, Gifu (JP)

(72) Inventors: Hironobu Murase, Gifu (JP); Motoaki Kuwahara, Gifu (JP); Masayuki Yamada, Gifu (JP)

(73) Assignee: CCI Corporation, Gifu (JP)

( * ) Notice: Subject to any disclaimer, the term of this patent is extended or adjusted under 35 U.S.C. 154(b) by 0 days. days.

(21) Appl. No.: 15/387,054

(22) Filed: Dec. 21, 2016

(65) Prior Publication Data

US 2017/0101661 A1 Apr. 13, 2017

Related U.S. Application Data

(63) Continuation of application No. 11/910,382, filed as application No. PCT/JP2006/306098 on Mar. 27, 2006, now abandoned.

(30) Foreign Application Priority Data

Mar. 29, 2005 (JP) .................. 2005-095169
Mar. 29, 2005 (JP) .................. 2005-096427

(51) Int. Cl.
*C12Q 1/00* (2006.01)
*G01N 27/30* (2006.01)
(Continued)

(52) U.S. Cl.
CPC .............. *C12Q 1/005* (2013.01); *C12N 11/08* (2013.01); *C12Q 1/004* (2013.01); *C12Q 1/61* (2013.01); *G01N 27/3272* (2013.01)

(58) Field of Classification Search
CPC .... G01N 27/125; G01N 27/226; G01N 27/30; G01N 27/302; G01N 27/308;
(Continued)

(56) References Cited

U.S. PATENT DOCUMENTS

| 4,371,612 A | 2/1983 | Matsumoto et al. |
| 4,576,913 A | 3/1986 | Adachi et al. |

(Continued)

FOREIGN PATENT DOCUMENTS

| JP | A-59210356 | 11/1984 |
| JP | A-59228158 | 12/1984 |

(Continued)

OTHER PUBLICATIONS

Nakako et al. (JP-62177443A, 1984) English Translation.*
(Continued)

*Primary Examiner* — Susan D Leong
(74) *Attorney, Agent, or Firm* — Cesari and McKenna, LLP (57) ABSTRACT

It is an object of the present invention to provide a sensor, which is capable of measuring, quickly and in high accuracy, concentration of neutral fat from a sample such as a biological sample or the like, without executing pretreatment of the sample. This object is attained by a biosensor for measuring concentration of neutral fat, based on value of current flowing in the electrode system, having: an insulating substrate; an electrode system having a working electrode and a counter electrode, formed onto the insulating substrate: and a reaction layer having a lipoprotein lipase, a glycerol dehydrogenase and an electron mediator, formed at the upper part or the vicinity of the electrode system.

16 Claims, 4 Drawing Sheets

(51) Int. Cl.
*C12Q 1/61* (2006.01)
*C12N 11/08* (2006.01)
*G01N 27/327* (2006.01)

(58) Field of Classification Search
CPC .. G01N 27/3275; G01N 33/49; G01N 33/491; G01N 33/50
See application file for complete search history.

(56) References Cited

U.S. PATENT DOCUMENTS

| | | | |
|---|---|---|---|
| 5,236,767 A * | 8/1993 | Torigoe | B41M 5/3825 428/200 |
| 5,346,819 A | 9/1994 | Adachi et al. | |
| 6,342,364 B1 | 1/2002 | Watanabe et al. | |
| 2002/0100684 A1 | 8/2002 | Bhullar et al. | |
| 2003/0082444 A1 | 5/2003 | Kuhr et al. | |
| 2004/0175196 A1 | 9/2004 | Yakamoto et al. | |
| 2005/0067303 A1 | 3/2005 | Wong et al. | |
| 2005/0072670 A1 * | 4/2005 | Hasegawa | C12Q 1/001 204/403.01 |
| 2005/0092097 A1 | 5/2005 | Shank et al. | |
| 2009/0001999 A1 | 1/2009 | Douglas | |
| 2010/0244655 A1 * | 9/2010 | Kim | H01B 1/24 313/346 R |

FOREIGN PATENT DOCUMENTS

| | | |
|---|---|---|
| JP | 62177443 A | 8/1987 |
| JP | A-3229144 | 10/1991 |
| JP | 8327553 | 12/1996 |
| JP | A-1151896 | 2/1999 |
| JP | A-2001/021526 | 1/2001 |
| JP | A-2001/343349 | 12/2001 |
| JP | A-2002/214188 | 7/2002 |
| JP | A-2004/233289 | 8/2004 |
| JP | A-2004/294231 | 10/2004 |

OTHER PUBLICATIONS

Takeshi et al. (JP2001343349, 2001) English Machine translation.*

Laurinavicius et al "Bioelectrochemical Application of Some PQQ-Dependent Enzymes" Bioelectrochemistry vol. 55, pp. 29-32, 2002.

Winartasaputra et al "Amperometric Enzymic Determination of Triglycerides in Serum" Analytical Chemistry vol. 54, pp. 1987-1990, 1982.

\* cited by examiner

BIOSENSOR

CROSS-REFERENCE TO RELATED APPLICATIONS

This application is a continuation of U.S. patent application Ser. No. 11/910,382, filed on Oct. 1, 2007, now abandoned, which was filed as a U.S. National Stage under 35 U.S.C. 371 of International Application No. PCT/JP2006/306098, filed on Mar. 27, 2006, which claims the benefit of Japanese Patent Application No. 2005-095169, filed Mar. 29, 2005, and Japanese Patent Application No. 2005-096427, filed Mar. 29, 2005. The contents of the prior applications are hereby incorporated by reference in their entirety.

TECHNICAL FIELD

The present invention relates to a biosensor, which is capable of determining, quickly and in high accuracy, quantity of neutral fat contained in a biological sample or the like.

BACKGROUND ART

In general, as a measurement method for neutral fat, there are (1) a method using chromotropic acid, (2) an acetylacetone method, (3) an enzyme method, and (4) a method using a nephelometer, however, any of these methods requires complicated analysis operations and long analysis time. Therefore, a biosensor has been developed, as a method for determining, simply and quickly, quantity of objective substances without execution of dilution or stirring of a sample liquid, in measurement of specific components contained in the sample.

As such a biosensor for measurement of neutral fat, there is a triglyceride sensor characterized in that a glycerol ester hydrolase is immobilized onto a porous polymer membrane or a hydrophilic uniform polymer membrane covered onto a gate insulating film of a pH sensitive, ion selective electric field effect transistor (JP-A-59-210356).

In addition, a neutral fat sensor using a lipoprotein lipase and a glycerol oxidase is also known (JP-A-59-228158). This sensor is one having a first electrode and a second electrode, and arranged with an immobilized enzyme at the vicinity of one electrode, so as to measure neutral fat contained in a solution to be measured, based on current flowing between membrane electrodes, and a lipoprotein lipase and a glycerol oxidase are used as the immobilized enzyme. However, this apparatus is complicated, because it is composed of a glass inner tube and a glass outer tube, and provided with a first electrode at the bottom of the inner tube; inner liquid is charged between the inner tube and the outer tube; and a second electrode is arranged in this inner liquid, which electrodes are immersed in a water tank maintained at 30° C., and a sample to be measured is charged in this water tank.

As a simpler and more convenient apparatus, a sensor for measuring substrate concentration of a sample liquid, by detecting electrochemically substance concentration change in a reaction among an enzyme, an electron mediator and a sample liquid by way of an electrode system, which has at least a measurement electrode and a counter electrode formed onto an insulating substrate, has been proposed (JP-A-2001-343349). This sensor is a sensor for measurement of neutral fat, which has a first layer formed onto a measurement electrode, by retaining a lipoprotein lipase, a glycerol kinase, a glycerophosphate oxidase and a surfactant, and by mounting a carrier through which a sample liquid can pass; and has a second layer formed onto a counter electrode, by retaining a surfactant, and by mounting a carrier through which a sample liquid can pass.

DISCLOSURE OF INVENTION

However, a triglyceride sensor described in the above JP-A-59-210356 measures fatty acids liberated by a glycerol ester hydrolase, using a pH sensitive, ion selective electric field effect transistor, and because response value is proportional to logarithm, of sample concentration, measurement accuracy is insufficient. And this sensor also has a problem that an apparatus becomes complicated.

In addition, a neutral fat sensor described in the above JP-A-59-228158 requires a heating apparatus to maintain temperature constant for accurate measurement. Since the sensor requires supply of a measurement sample from its outside, it requires a large quantity of samples, thus makes measurement difficult using a small amount of a sample.

Further, a sensor described in the above JP-A-2001-343349, is configured by different layers for an enzyme and an electron mediator, which makes an apparatus extremely complicated, and requires use of two kinds of expensive enzymes, a glycerol kinase and a glycerophosphate oxidase, as well as a lipoprotein lipase.

Recently, the number of patients of hyperlipemia, which is a lifestyle-related disease, has been growing steadily, and thus it is a present state that development of a sensor, which is capable of measuring, quickly and in high accuracy, concentration of neutral fat contained in a sample like blood or the like, is strongly desired.

In these circumstances, it is an object of the present invention to provide a sensor I which is capable of measuring, quickly and in high accuracy, concentration of neutral fat from a sample like a biological sample or the like, without executing pretreatment of the sample.

The present inventors have found that, in a biosensor for measuring concentration of neutral fat, based on value of current flowing in the electrode system, having: an insulating substrate; an electrode system having a working electrode and a counter electrode, formed onto the insulating substrate; and a reaction layer formed at the upper part or the vicinity of the electrode system; by inclusion of a lipoprotein lipase, a glycerol dehydrogenase and an electron mediator in the reaction layer, concentration of glycerol in a sample can be measured rapidly and in high accuracy, and have thus completed the present invention.

Namely, one aspect of the present invention relates to a biosensor for measuring concentration of neutral fat, based on value of current flowing in the electrode system, having: an insulating substrate; an electrode system having a working electrode and a counter electrode, formed onto the insulating substrate; and a reaction layer having a lipoprotein lipase, a glycerol dehydrogenase and an electron mediator, formed at the upper part or the vicinity of the electrode system.

Further other objects, features and characteristics of the present invention will be made clear by referring to preferable embodiments that will be exemplified in explanation hereafter and accompanying drawings.

DETAILED DESCRIPTION

Explanation will be given below on one preferable embodiment for carrying out the present invention, however, technical scope of the present invention should not be limited only to the following embodiment.

One aspect of the present invention relates to a biosensor for measuring concentration of neutral fat, based on value of current flowing in the electrode system, having: an insulating substrate; an electrode system having a working electrode and a counter electrode, formed onto the insulating substrate; and a reaction layer having a lipoprotein lipase, a glycerol dehydrogenase and an electron mediator, formed at the upper part or the vicinity of the electrode system.

Figure 1:
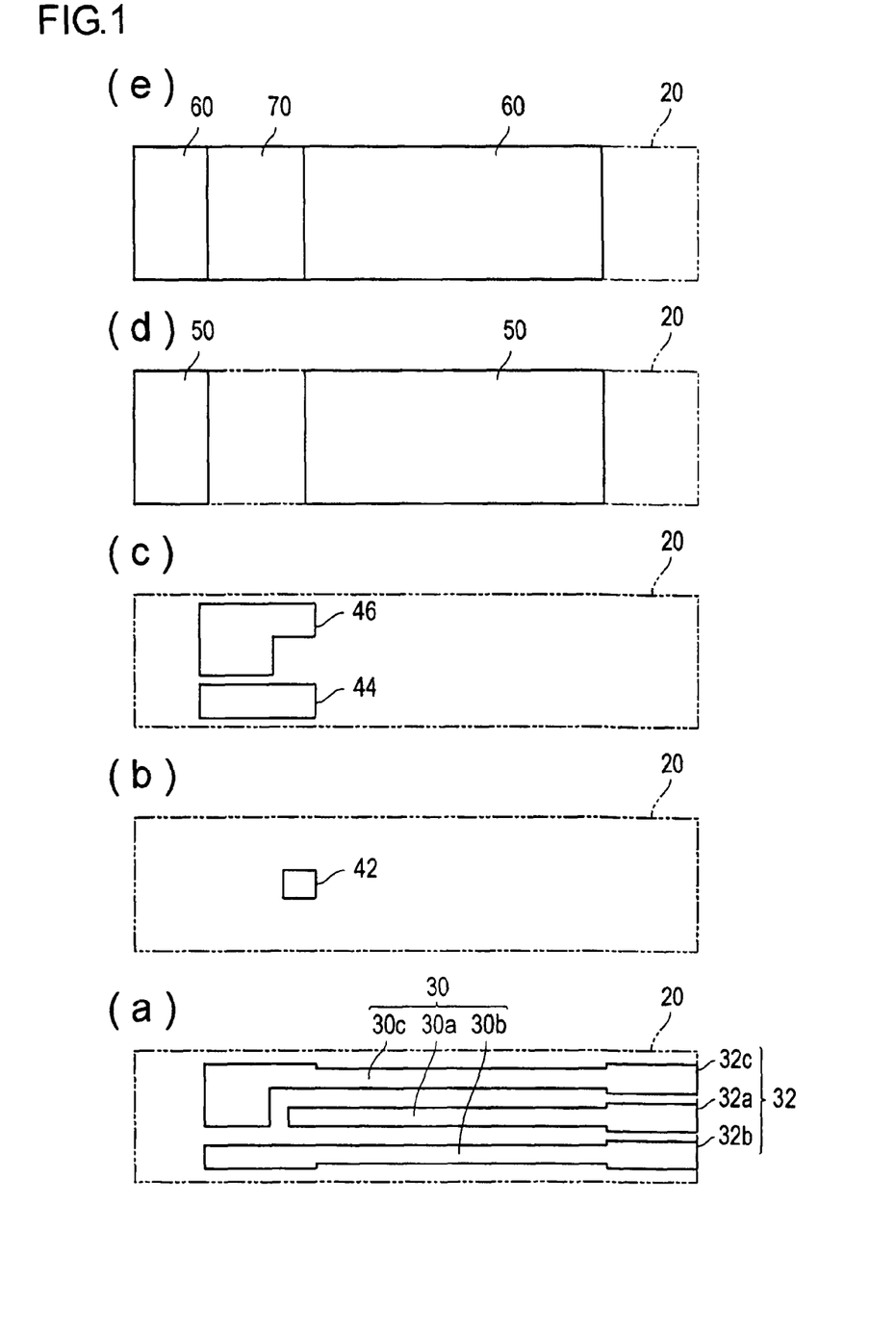
FIG. 1 is a plan view showing a formation pattern of each of the configuration elements of a biosensor of the present invention; (a) is a plan view showing a formation pattern of a lead part and a connector part on an insulating substrate; (b) is a plan view showing a formation pattern of a reference electrode configuring an electrode system; (c) is a plan view showing a formation pattern of a working electrode and a counter electrode configuring an electrode system; (d) is a plan view showing a formation pattern of an insulating layer; and (e) is a plan view showing a formation pattern of a spacer and a reaction layer.

FIG. 1 is a plan view showing a formation pattern of each of the configuration elements of the biosensor 10 of the present invention. In each of the drawings of FIG. 1, a virtual line showing an outer shape of the insulating substrate 20 is shown in addition to configuration elements for explanation purpose by each of the drawings. FIG. 1 (a) is a plan view showing a formation pattern of the lead part 30 and the connector part 32 on the insulating substrate 20; FIG. 1 (b) is a plan view showing a formation pattern of the reference electrode 42 configuring an electrode system 40 (see FIGS. 2 and 3); FIG. 1 (c) is a plan view showing a formation pattern of the working electrode 44 and the counter electrode 46 configuring the electrode system 40; FIG. 1 (d) is a plan view showing a formation pattern of the insulating layer; and FIG. 1 (e) is a plan view showing a formation pattern of the spacer 60 and the reaction layer 70. It should be noted that, in each of the drawings of FIG. 1, configuration elements for explanation purpose by each of the drawings, and the insulating substrate 20 are shown. FIG. 3 is a plan view showing the biosensor 10 formed by each of the configuration elements shown in each of the drawings of FIG. 1. In the biosensor 10 shown in FIG. 2, the integrated lead part 30 and the connector part 32, the electrode system 40, the insulating layer 50, the spacer 60 and the reaction layer 70 are laminated onto the insulating substrate 20, from the side of the insulating substrate 20, in this order. It should be noted that the biosensor 10 may be used and stored in a state of being further covered with a cover, however, in FIG. 1 and FIG. 2, drawing of such a cover is omitted. In addition, for convenience of explanation, dimension ratio in the drawings is magnified, and the embodiment shown may be different from the practical scale.

The biosensor 10 is an apparatus to measure concentration of neutral fat in a sample like body fluid or the like.

Explanation will be given in detail below on each of the parts configuring the biosensor 10.

The biosensor 10 is provided with the insulating substrate 20 as a substrate thereof. The insulating substrate 20 may be configured by a conventionally well-known insulating material such as a resin, for example, polyethylene terephthalate (PET), polyethylene or the like; glass, ceramics, paper; or the like. The shape or size of the insulating substrate 20 is not especially limited.

Figure 2:
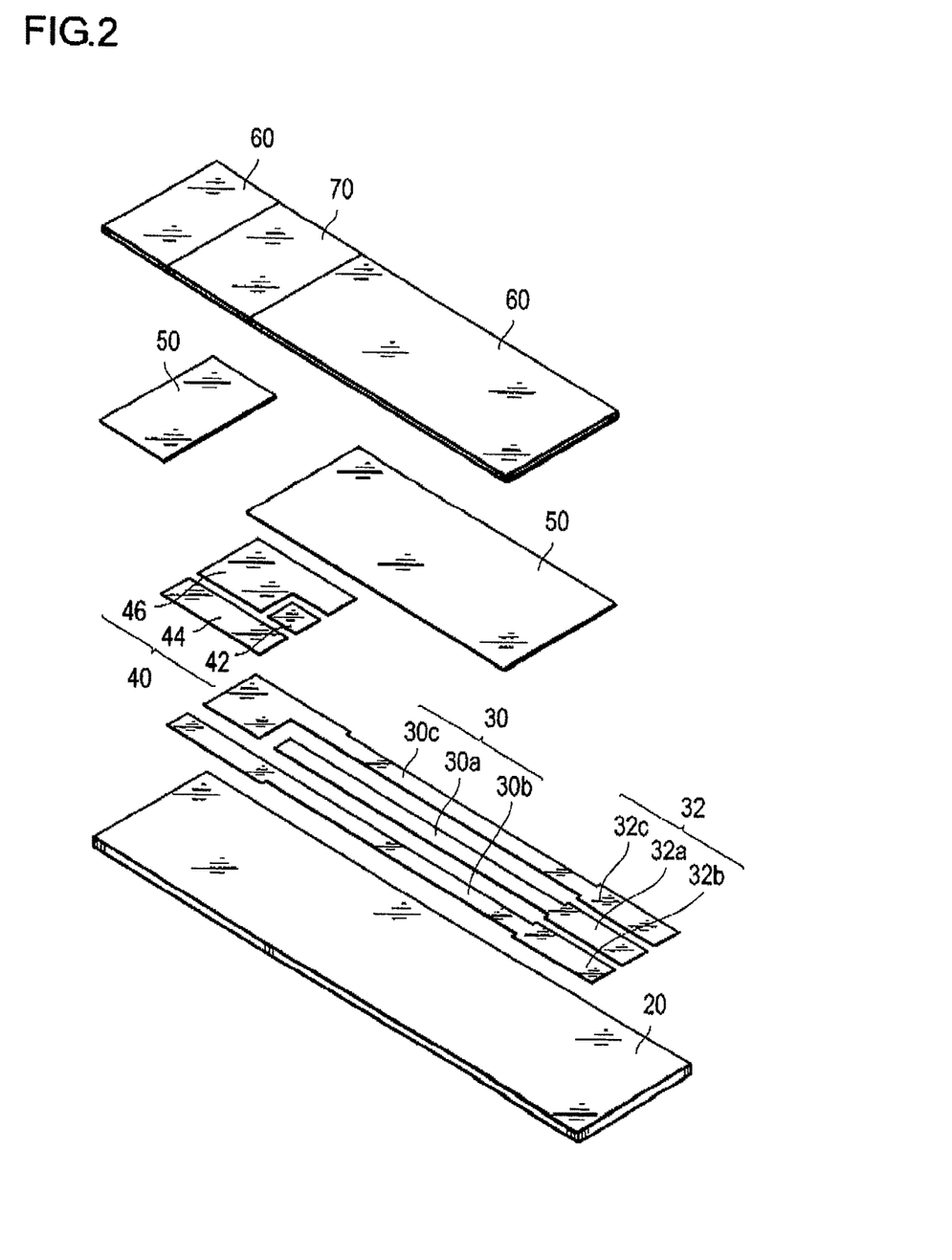
FIG. 2 is an exploded perspective view showing lamination order of each of the configuration elements shown in each of the drawings of FIG. 1.
Figure 3:
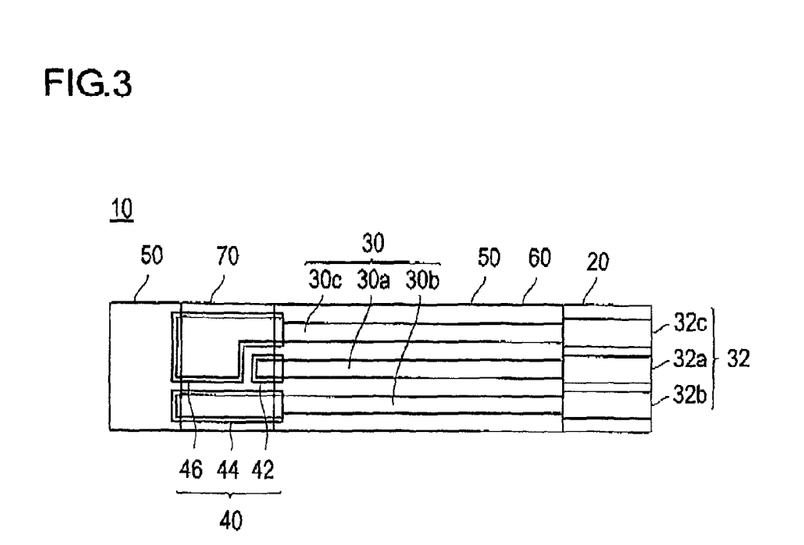
FIG. 3 is a plan view showing a biosensor formed by each of the configuration elements shown in each of the drawings of FIG. 1 and FIG. 2.

Onto the insulating substrate 20, as shown in FIG. 1 and FIG. 2, the lead parts (30$a$, 30$b$ and 30$c$) and the connector parts (32$a$, 32$b$ and 32$c$) are formed. The connector parts (32$a$, 32$b$ and 32$c$) function as means for electrically connecting the electrode system 40, to be described later, and the exterior of the biosensor 10, and are electrically connected with the electrode system 40 via the lead parts (30$a$, 30$b$ and 30$c$). The lead parts (30$a$, 30$b$ and 30$c$) are extended, as shown in FIG. 2, from the connector parts (32$a$, 32$b$ and 32$c$) to the position of the electrode system 40, thus configure a foundation layer of each of the electrodes (42, 44 and 46) of the electrode system 40. A material configuring the lead parts (30$a$, 30$b$ and 30$c$) and the connector parts (32$a$, 32$b$ and 32$c$) is not especially limited, and a material conventionally used in formation of the lead part and the connector part of a biosensor may be used as appropriate. However, in view of further enhancing response sensitivity of the biosensor 10, the lead parts (30$a$, 30$b$ and 30$c$) and the connector parts (32$a$, 32$b$ and 32$c$) are preferably configured by a material with smaller surface resistivity value. Specifically, it is preferable to be configured by a material having a surface resistivity value of equal to or smaller than 50 m$\Omega$/$\square$, more preferably equal to or smaller than 40 m$\Omega$/$\square$, in a thickness of 10 μm. Configuration of the lead part and the connector part, using a material with surface resistivity value larger than the above range, reduces linearity between substrate concentration and response value, which could provide insufficient enhancement effect of measurement sensitivity by the present invention. On the other hand, the lower limit of the surface resistivity value of this material is not especially limited, however, in consideration of the addition of a binder to secure adhesion of the lead part 30 and the connector part 32 with a substrate, it is predicted that the surface resistivity value of the lead part 30 and the connector part 32 is about 0.1 m m$\Omega$/$\square$ or higher, in a thickness of 10 μm. However, the lead part 30 and the connector part 32 may be naturally configured by a material having the surface resistance value outside this range. As the material having the preferable surface resistivity value, as described above, for example, one made of metals such as silver, gold, platinum, palladium and the like, as a major component, is included. The material configuring each of the lead parts (30$a$, 30$b$ and 30$c$) and each of the connector parts (32$a$, 32$b$ and 32$c$) may be the same, or may be different. However, in view of low cost, it is preferable that both of the lead part and the connector part are configured by silver. A method for formation of the lead part and the connector part is not especially limited, and they can be formed by a conventionally known method such as a screen printing method, a sputtering method or the like. In this case, the material configuring the lead part and the connector part may be supplied in a form of paste containing a binder of a resin such as polyester or the like. After formation of a coated film by the above method, it is preferable to be subjected to heating processing at a temperature of about 50 to 200° C. to harden the coated film.

As shown in FIG. 1 and FIG. 2, onto the upper layer of a foundation layer, to which the lead parts (30$a$, 30$b$ and 30c) are extended, the electrode system 40 is formed. This electrode system 40 functions, in using the biosensor 10, as a voltage application means for applying voltage on a sample in the reaction layer 70, to be described later, and an current detection means for detecting current flowing in a sample.

In the embodiment shown by the drawing, the electrode system 40 is configured by three electrodes: the reference electrode 42, the working electrode 44 and the counter electrode 46. Namely, the biosensor 10 of the embodiment shown is a three-electrode system sensor. However, the biosensor of the present invention is not limited to a three-electrode system sensor, and a two-electrode system sensor provided with an electrode system not containing a reference electrode may be included. It should be noted that, in view of executing voltage control in the electrode system 40 in higher sensitivity, a three-electrode system is used more preferably than a two-electrode system.

The working electrode 44 and the counter electrode 46 function as current measurement means, as a pair, for measuring oxidation current (response current) flowing in application of voltage on a sample in the reaction layer 70, to be described later. In using the biosensor 10, predetermined voltage is applied between the reference electrode 42 and the working electrode 44. A material configuring each of the electrodes is not especially limited, and a material conventionally used in formation of the electrode system of a biosensor may be used as appropriate. However, in view of further enhancing response sensitivity of the biosensor 10, the electrode system 40 is preferably configured by a material with a surface resistivity value of equal to or smaller than 100Ω/□, more preferably equal to or smaller than 80Ω/□, in a thickness of 10 μm. Configuration of the electrode system 40, using a material with surface resistivity value larger than the above range, reduces linearity between substrate concentration and response value, which could provide insufficient enhancement effect of measurement sensitivity by the present invention. On the other hand, the lower limit of the surface resistivity value of this material is not especially limited. The material configuring each of the electrodes (42, 44 and 46) may be the same, or may be different. However, in view of corrosion resistance and cost, it is preferable that each of the electrodes (42, 44 and 46) is configured by carbon, as a main component. However, in some cases, the electrode system 40 may be configured by a material other than carbon, such as various metals or the like. A method for formation of the electrode system is not especially limited, and it can be formed by a conventionally known method such as a screen printing method, a sputtering method or the like. In this case, the material configuring the electrode system may be supplied in a form of paste containing a binder of a resin like polyester or the like. After formation of a coated film by the above method, it is preferable to be subjected to heating processing to harden the coated film.

In the biosensor 10 of the present embodiment, each of the electrodes (42, 44 and 46) configuring the electrode system 40 is exposed, as shown in FIG. 3, from a nearly rectangular-shaped opening part, which the insulating layer 50 formed onto the upper layer of the electrode system 40 has. Here, value of exposed area ratio of the working electrode 44 and the counter electrode 46 from the opening part is preferably controlled within a predetermined range. Specifically, exposed area from the opening part of the counter electrode 46 is 1.2 to 3.0 times as large as exposed area from the opening part of the working electrode 44. Exposed area of the counter electrode 46 below 1.2 times as large as exposed area of the working electrode 44, provides insufficient control of saturation of a redox reaction at the counter electrode 46, in measurement of oxidation current value, which could provide insufficient effect of the present invention that measurement sensitivity of the biosensor 10 is enhanced. On the other hand, exposed area of the counter electrode 46 over 3.0 times as large as exposed area of the working electrode 44, could make compact sizing of the biosensor 10 difficult.

Onto the lead parts (30a, 30b and 30c) and the connector parts (32a, 32b and 32c) formed onto the insulating substrate 20, along with onto the upper layer of the electrode system 40, as shown in FIG. 1 and FIG. 2, the insulating layer 50 is formed so that the electrode system 40 is exposed. The insulating layer 50 functions as an insulation means for preventing short circuit between each of the electrodes configuring the electrode system 40. A material configuring the insulating layer 50 is not especially limited, and for example, it may be configured by resist ink; a resin such as PET, polyethylene or the like; glass, ceramics, paper or the like. A method for formation of the insulating layer 50 is not especially limited, and it can be formed by a conventionally known method such as a screen printing method, an adhesion method or the like.

Onto the upper layer of the electrode system 40 and the insulating layer 50, as shown in FIG. 1 and FIG. 2, the spacer 60 and the reaction layer 70 are formed. In using the biosensor 10, an enzymatic reaction, to be described later, proceeds in the reaction layer 70. In addition, mounting of the spacer 60 prevents leakage of the reaction layer 70 and a sample solution in using the biosensor 10. In the embodiment shown by the drawing, the spacer 60 has a rectangular opening part at the position corresponding to the electrode system 40, and the reaction layer 70 is provided onto this opening part. However, the shape of the opening part, which the spacer 60 has, is not limited to rectangle and an arbitrary shape may be used. A material configuring the spacer 60 is not especially limited; for example, it is configured by a resin such as PET, polyethylene or the like; glass, ceramics, paper or the like. A method formation of the spacer 60 and the reaction layer 70 is not especially limited, and for example, a method for mounting the spacer 60 having an opening part at a predetermined position, followed by dropping of a solution for forming the reaction layer 70 at this opening part, and drying can be used.

In the biosensor of the present embodiment, the reaction layer 70 has a lipoprotein lipase, a glycerol dehydrogenase and an electron mediator.

Conventionally, there has been a biosensor formed with an electrode system having a working electrode and a counter electrode, onto the insulating substrate; and a reaction layer formed at the upper part or the vicinity of the electrode system, and a sensor by combination of a lipoprotein lipase with other enzymes at the reaction layer was also present. However, in the present invention, formulation of a glycerol dehydrogenase together with a lipoprotein lipase is capable of measuring neutral fat conveniently and inexpensively. In addition, because the reaction layer further contains an electron mediator, it is not necessary to separately mount a reaction layer containing an enzyme, and a layer containing an electron mediator, which is capable of making a structure simple. The addition of a sample containing lipoprotein to the biosensor of the present embodiment liberates glycerol and fatty acid, by decomposition of neutral fat in lipoprotein by a lipoprotein lipase contained in the reaction layer. In addition, presence of a glycerol dehydrogenase and an electron mediator in the reaction layer oxidizes glycerol and at the same time reduces the electron mediator. Therefore, concentration of a substrate can be accurately determined by oxidation current value of the resultant electron mediator. Explanation will be given below in detail on characteristic configuration of the present invention.

The lipoprotein lipase used in the biosensor of the present embodiment is not especially limited as long as being capable of liberating glycerol by decomposition of lipoprotein, and any of a conventional lipoprotein lipase or one with enhanced stability or reactivity by further modification thereof may be preferably used. Content of such a lipoprotein lipase in the reaction layer may be selected as appropriate by kind of a biological sample to be used, or addition amount thereof. In general, amount of the lipoprotein lipase contained in the reaction layer is 0.001 to 1000 units of activity, more preferably 0.1 to 500 units of activity, and particularly preferably 0.1 to 300 units of activity. It should be noted that definition and a method for measuring the unit of activity of the lipoprotein lipase are as follows:

(A Measurement Method for Activity of the Lipoprotein Lipase)

Into 1 mL of 20 mM phosphate buffer solution (pH 7), 2 mL of soybean oil emulsion was added, and stirred sufficiently; subsequently, 1 mL of a solution containing a lipoprotein lipase is added and shaken at 37° C. for 20 minutes. After the shaking, 10 mL of a reaction termination solution was added, and further 6 mL of n-heptane and 4 mL of ion-exchanged water were added and sufficiently stirred. It should be noted that "soybean oil emulsion" is one prepared by adding 24 mL of soybean oil to 16 mL of a 10% bovine serum albumin solution prepared by 20 mM phosphate buffer solution (pH 7), and stirring sufficiently. In addition, "a reaction termination solution" is a mixture liquid of n-heptane/2-propanol/2N sulfuric acid (10/40/1, w/w/w).

Then, 6 mL of the upper layer (n-heptane layer) is taken, 2 drops of a cresol red indicator are dropped therein, and is titrated by an ethanol solution of 0.01 M potassium hydroxide to determine amount of liberated fatty acid, by judging time when the liquid turns purple as an end point. As a blank test, similar operation is executed using 1 mL of a 20 mM phosphate buffer solution instead of a solution containing the lipoprotein lipase, to determine liberated fatty acid.

Under the above condition, amount of the lipoprotein lipase liberating 1 µmol of fatty acid in 1 minute is defined as 1 unit of activity.

Similarly, a glycerol dehydrogenase is not especially limited as long as being capable of reducing the electron mediator by oxidation of glycerol, and any of a conventional glycerol dehydrogenase or one with enhanced stability or reactivity by further modification thereof may be preferably used. In particular, it is preferable that the glycerol dehydrogenase is a coenzyme dependent type.

As such a coenzyme, a quinone coenzyme such as pyrrolo-quinoline quinone (PQQ), CoQ or the like; a vitamin coenzyme such as flavin adenine dinucleotide (FAD), FMN, NAD, NADP, biotin or the like; or the like can be preferably used. Among these, the coenzyme is preferably PQQ or FAD, and PQQ is more preferable. Here, for example, containing the glycerol oxidase in a reaction layer, as an enzyme, makes correct measurement of neutral fat difficult, because a reaction proceeds by using dissolved oxygen in a solution. On the other hand, by using the biosensor of the above-described embodiment, there is no effect of dissolved oxygen, because the coenzyme dependent type glycerol dehydrogenase only uses an electron mediator in a solution for a reaction. Therefore, measurement of oxidation current obtained by oxidation of a reduced electron mediator is capable of providing concentration of glycerol accurately. Content of the glycerol dehydrogenase in the reaction layer may be selected as appropriate by kind of a biological sample to be used, or addition amount thereof. In general, amount of the glycerol dehydrogenase contained in the reaction layer is 0.001 to 200 units of activity, more preferably 0.05 to 100 units of activity, and particularly preferably 0.1 to 80 units of activity. It should be noted that as for definition and a method for measuring the unit of activity of the glycerol dehydrogenase, description of examples to be described later, can be referred to.

The glycerol dehydrogenase used in the present embodiment may be used as a product purchased on the market, or may be one prepared per se. A method for preparing per se the enzyme includes, for example, a method for utilizing bacteria producing the enzyme. The bacteria producing the enzyme include, for example, those belonging to various genera such as *Gluconobacter, Pseudomonas*, and the like. In the present embodiment, in particular, a PQQ dependent glycerol dehydrogenase present in a membrane fraction of bacteria belonging to *Gluconobacter* can be preferably used. Furthermore, in view of easy availability, *Gluconobacter*, particularly, *Gluconobacter oxydans* NBRC 3171, 3253, 3258, 3285, 3289, 3290, 3291; *Gluconobacter frateurii* NBRC 3251, 3260, 3264, 3265, 3268, 3286; *Gluconobacter cerinus* NBRC 3262; or the like can be used. A representative strain of such microorganisms includes *Gluconobacter oxydans* NBRC 3291.

A method for obtaining the PQQ dependent glycerol dehydrogenase from these bacteria is not especially limited, and conventionally known knowledge may be referenced as appropriate.

In the case where the glycerol dehydrogenase in the biosensor of the present embodiment is PQQ dependent, it is preferable that the glycerol dehydrogenase is modified glycerol dehydrogenase obtained by chemical modification with a bivalent cross-linking reagent under presence of a surfactant. In such modified glycerol dehydrogenase, a hydrophobic enzyme has a firm structure by being introduced with a cross-linked structure without aggregation, and is thus capable of enhancing heat stability. Therefore, by using the biosensor of the above-described embodiment, it is possible to measure neutral fat in a sample in high accuracy.

The bivalent cross-linking agent is not especially limited, as long as being capable of introducing a cross-linked structure by a reaction with an amino group or the like contained in the PQQ dependent glycerol dehydrogenase: and a dialdehyde compound, a dicarboxylic acid compound, a diisocyanate-based compound, an imidate compound or the like, which can be used as a cross-linking agent in a field of an immobilized enzyme, can be preferably used. The dialdehyde compound includes glutaric aldehyde, succinic dialdehyde, adipic aldehyde or the like; the dicarboxylic acid compound includes adipic acid, dimethyladipic acid or the like; the diisocyanate-based compound includes hexamethylene diisocyanate, toluene diisocyanate or the like; and the imidate compound includes dimethyl suberimidate, dimethyl pimelimidate or the like. In the present invention, among the above bivalent cross-linking agents, glutaric aldehyde is particularly preferable.

On the other hand, a surfactant is not especially limited, as long as one used generally for solubilization of membrane protein, and conventionally known knowledge can be referenced as appropriate. For example, Triton X-100, octyl glucoside, sodium cholate or the like is included.

Reaction temperature in a cross-linking reaction may be selected as appropriate in response to the bivalent cross-linking agent to be used, and generally, the reaction is preferably executed at about 0 to 40° C.; and reaction time is 1 minute to 4 hours, preferably about 5 minutes to 2 hours, particularly preferably 5 minutes to 1 hour. The reaction time below 1 minute provides insufficient cross-linking and increases amount of uncross-linked enzyme, while the reaction time over 4 hours excessively increases cross-linking rate, and enzymatic activity may be lost.

The cross-linking reaction can be terminated by the addition of a termination agent such as a glycine solution or a Tris-hydrochloride buffer solution. After the above cross-linking processing, unreacted glycine, the bivalent cross-linking agent, 2-amino-2-hydroxymethyl-1,3-propanediol and a reaction product between a termination agent and a bivalent cross-linking reagent can be removed by execution of a dialysis method, a chromatography method, an ultra-filtration method or the like. In the present invention, execution of a dialysis method is particularly preferable, because operation thereof is simple and convenient and requires less cost.

An electron mediator receives electrons generated by action of a redox enzyme, namely is reduced, in using the biosensor 10. Thus reduced electron mediator is electrochemically oxidized by current flowing in the electrode system 40, after completion of an enzymatic reaction. Concentration of a desired component in a sample solution can be calculated from value of current (referred to as oxidation current) flowing in this reaction.

An electron mediator used in the biosensor of the present embodiment is also not especially limited, as long as being reduced accompanied with oxidation of glycerol by the glycerol dehydrogenase, and oxidized by application of voltage on the electrode system. Specifically, for example, a ferricyanide ion, p-benzoquinone, a p-benzoquinone derivative, phenazine methosulfate, a phenazine methosulfate derivative, methylene blue, thionin, indigocarmine, gallocyanin, safranin, ferrocene and a derivative thereof, a-naphthoquinone and an a-naphthoquinone derivative are illustrated. Here, a p-benzoquinone derivative, a phenazine methosulfate derivative, or an a-naphthoquinone derivative includes p-benzoquinone, phenazine methosulfate or a-naphthoquinone bonded with an alkyl group having 1 or 2 carbon atoms, an alkoxyl group having 1 or 2 carbon atoms, a halogen atom such as a fluorine atom, a chlorine atom, a bromine atom or the like is included. It should be noted that in the case where the above-described PQQ dependent type glycerol dehydrogenase is contained in a reaction layer as the glycerol dehydrogenase, phenazine methosulfate; 1-methoxy-5-methylphenazinium methylsulfate as a phenazine methosulfate derivative; p-benzoquinone; 2-methyl-1,4-benzoquinone as a p-benzoquinone derivative; and a-naphthoquinone are preferably adopted as an electron mediator.

In addition, these electron mediators may be used alone, or may be used two or more kinds by combination with 1-methoxy-5-methylphenazinium methylsulfate and a ferricyanide ion, or the like.

Concentration of an electron mediator in the reaction layer can be selected as appropriate in response to kind of a redox enzyme to be used, or a target sample, or the addition amount thereof or the like, however, in general, in the case where a 0.5 to 10 μL of sample is added, it is preferably 0.01 to 1000 μg, more preferably 0.1 to 100 μg, and particularly preferably 1 to 50 μg per one sensor.

It is preferable that the reaction layer further contains a surfactant and a pH buffering agent. Reason for this is as follows: The biosensor of the present embodiment is used aiming at measurement of concentration of neutral fat contained in a sample; therefore, a sample to be dropped onto the sensor contains neutral fat, which is an oil soluble substance; here, according to a present embodiment wherein a reaction layer further contains a surfactant and a pH buffering agent, lowering of measurement sensitivity caused by oil solubility of neutral fat in a sample can be suppressed. Explanation will be given in detail below on the above-described embodiment.

In the biosensor of the present embodiment, the reaction layer 70 contains a surfactant. Containing the surfactant in the reaction layer 70 accelerates dissolution of neutral fat contained in a sample into the reaction layer 70. As a result, a biosensor excellent in measurement sensitivity can be provided.

Kind of the surfactant contained in the reaction layer 70 is not especially limited, and a conventionally known surfactant may be used. Here, the surfactant is broadly classified into a cationic surfactant, an anionic surfactant, an amphoteric surfactant, and a nonionic surfactant, and any of these may be used. Here, as the cationic surfactant, acetyl trimethyl ammonium salt, a dodecyl trimethyl ammonium salt or the like is included; as the anionic surfactant, sodium alkylsulfate, an alkylbenzene sulfonic acid salt, a cholic acid salt or the like is included; as the amphoteric surfactant, lecithin, phosphatidylethanolamine, lysolecithin or the like is included; and as the nonionic surfactant, acylsorbitan, alkyl glucoside, a Tween-based surfactant, a Triton-based surfactant, a Brij-based surfactant or the like is included. It is natural that surfactants other than these may be used. Among these, preferably a nonionic surfactant, more preferably a Tween-based surfactant or a Triton-based surfactant is used.

Content of the surfactant in the reaction layer 70 is not especially limited, and can be adjusted as appropriate in response to amount or the like of an oil soluble substance in a sample solution. As an example, in the reaction layer 70 of the biosensor 10 used by the addition of 0.5 to 10 μL of a sample solution, usually 0.1 to 500 μg, preferably 1 to 100 μg, and more preferably 1 to 50 μg of the surfactant is contained.

In addition, in the biosensor 10 of the present embodiment, the reaction layer 70 contains the pH buffering agent. Containing the pH buffering agent in the reaction layer 70 further enhances sensitivity of the biosensor 10. Reason for this is estimated to be as follows. Namely, in dissolution of the reaction layer 70 by the addition of a sample solution, pH of the reaction layer 70 may be varied depending on the composition of the sample solution. As an example of the pH variation, in the reaction layer 70, reduction of pH accompanying with liberation of fatty acid, caused by decomposition of neutral fat in a sample, is included. Here, because mechanism of the biosensor 10 is indirect determination of amount of a substrate oxidized by a redox enzyme, variation of pH in the reaction layer 70 results in difference between pH of the reaction layer 70, and optimal pH of the enzyme depending on kind of the enzyme, which may lead to lowering of measurement sensitivity of a sensor. On the other hand, containing of the pH buffering agent by the reaction layer 70 suppresses such pH variation, and prevents lowering of measurement sensitivity of a sensor accompanied by pH variation.

Kind of the pH buffering agent contained in the reaction layer 70 is not especially limited, and may be selected as appropriate in response to optimal pH of an enzyme to be used, and as an example, glycine-Hel, glycine-NaOH, citric acid-sodium citrate, MES-NaOH, MOPS-NaOH, phosphoric acid, Tris-HCl, acetic acid or the like is included. It should be noted that pH of the pH buffering agent is preferably 6 to 9. In addition, these pH buffer agents may be contained alone in the reaction layer 70, or two or more kinds may be contained in combination, in the reaction layer 70. It is natural that a pH buffer agent other than these may be contained in the reaction layer 70.

The reaction layer may further contain other components. As the other components, for example, a hydrophilic polymer or an enzyme stabilizer or the like is included.

Containing of the hydrophilic polymer in the reaction layer is capable of preventing peeling of the reaction layer from the surface of the electrode system. In addition, the hydrophilic polymer has effect of preventing crack of the surface of the reaction layer, and is effective in enhancing reliability of the biosensor. Furthermore, it is also capable of suppressing adsorption of an adsorbent component like protein or the like onto the electrode system 40. Such hydrophilic polymer is not especially limited, and for example, cellulose, guar gum, carboxymethyl cellulose, hydroxyethyl cellulose, hydroxypropyl cellulose, methyl cellulose, ethyl cellulose, carboxymethyl ethyl cellulose, polyvinylpyrrolidone, polyvinylalcohol, polyamino acid such as polylysine, polystyrene sulfonic acid, gelatin, acrylic acid and a salt thereof, methacrylic acid and a salt thereof, starch, maleic anhydride and a salt thereof, agarose gel, tannic acid, pectin, casein, carrageenan, furcellaran, pullulan, collagen, chitin, chitosan, sodium chondroitin sulfate, lignin sulfonic acid, polyacrylamide, polyethylene glycol, and derivatives thereof are included. Containing tannic acid, pectin, casein, carrageenan, furcellaran, pullulan, collagen, chitin, chitosan, sodium chondroitin sulfate, lignin sulfonic acid, and a derivative thereof, among these, in the reaction layer 70 further suppresses adsorption of an adsorbent component onto an electrode; tannic acid, pectin, casein and derivatives thereof can be particularly preferably used. It should be noted that these hydrophilic polymers may be contained alone in the reaction layer 70, or two or more kinds may be contained in combination, in the reaction layer 70. It should be noted that formulation amount of such a hydrophilic polymer is, in general, preferably 0.1 to 1000 μg, more preferably 1 to 500 μg, and particularly preferably 5 to 100 μg, per one sensor.

The reaction layer 70 may be a layer configured by a single layer, or may be a layer configured by two or more layers. As an example of the embodiment wherein the reaction layer 70 is configured by two layers, for example, an embodiment, wherein the reaction layer 70 is configured by a first reaction layer having the electron mediator and the hydrophilic polymer, but substantially not having the glycerol dehydrogenase; and a second reaction layer formed onto the upper layer of the first reaction layer, and having the glycerol dehydrogenase and the hydrophilic polymer, but substantially not having the electron mediator, is included. In addition, as an example of the embodiment wherein the reaction layer 70 is configured by three layers, for example, an embodiment, wherein the reaction layer 70 is configured by a first reaction layer having the electron mediator and the hydrophilic polymer, but substantially not having the glycerol dehydrogenase; a second reaction layer formed onto the upper layer of the first reaction layer, and having the hydrophilic polymer, but substantially not having the glycerol dehydrogenase and the electron mediator; and a third reaction layer formed onto the upper layer of the second reaction layer, and having the glycerol dehydrogenase and the hydrophilic polymer, but substantially not having the electron mediator, is included.

In addition, the reaction layer 70 is formed onto the upper layer of the electrode system 40 in the embodiment shown in the drawing, however, in some cases, unlike the embodiment shown in the drawing, the reaction layer 70 may be formed, at the vicinity of the electrode system 40, as the embodiment where the electrode system 40 and the reaction layer 70 do not directly contact each other. It should be noted that, as the embodiment where the reaction layer 70 is formed at "the vicinity" of the electrode system 40, an embodiment where space or a filter is intervenient between the electrode system 40 and the reaction layer 70, or an embodiment where the reaction layer 70 is formed between a sample supply port and the electrode system 40 is exemplified.

Explanation was given in detail above on configuration of the biosensor 10 of the present invention, however, the configuration is not limited to the above Embodiment, and various improvements may be executed with reference to conventionally known knowledge as appropriate. As the conventionally known knowledge, for example, JP-A-2-062952, JP-A-S-87768, JP-A-II-201932 or the like is included.

Now explanation will be given on action of the biosensor 10 of the present invention.

First of all, a predetermined amount of a sample containing a component, whose concentration is desired to be measured, is supplied to the reaction layer 70 of the biosensor 10. The specific embodiment of the sample is not especially limited, and a solution containing neutral fat, as a substrate of glycerol dehydrogenase used for the biosensor 10, can be used as appropriate. As the sample, for example, a biological sample such as blood, urine, saliva or the like; foods such as fruits, vegetables, raw materials of processed foods and the like; or the like is used. However, other solutions may also be used as the sample. In addition, use of a sample solution with, in particular, high content of neutral fat is capable of further eliciting effect of the present invention. It should be noted that, as the sample, a stock solution may be used without dilution, or a solution diluted with a suitable solvent may also be used, aiming at adjustment of viscosity or the like. An embodiment for supplying the sample to the reaction layer 70 is not especially limited, and a predetermined amount of the sample may be supplied by dropping vertically and directly to the reaction layer 70, or the sample may be supplied from a horizontal direction to the reaction layer 70, by a sample supply means separately provided.

When a sample is supplied to the reaction layer 70, neutral fat, which is a substrate in the sample, is decomposed into glycerol and fatty acid, by action of the lipoprotein lipase contained in the reaction layer 70. Then, liberated glycerol is oxidized by action of the glycerol dehydrogenase, and emits electrons at the same time of oxidation of itself. The electrons emitted from the substrate are captured by an electron mediator, and the electron mediator itself changes from an oxidized type to a reduced type, accompanying therewith. After the addition of the sample, while leaving of the biosensor 10 as it is, for a predetermine time, neutral fat in the sample is completely oxidized, by action of the lipoprotein lipase and the glycerol dehydrogenase, and a certain amount of the electron mediators are converted from an oxidized type to a reduced type. Time for leaving to complete a reaction between neutral fat in the sample and an enzyme is not especially limited, however, the biosensor 10 may be left usually for 0 to 5 minutes, preferably for 0 to 3 minutes, after the addition of the sample.

Subsequently, aiming at oxidization of the reduced type electron mediator, predetermined voltage is applied between the working electrode 44 and the counter electrode 46 via the electrode system 40. This voltage application makes current (hereafter may also be referred to as "oxidation current") flow in the reaction layer 70, and by this current the reduced type electron mediator is in turn electrochemically oxidized and converted to the oxidized type. Amount of the reduced type electron mediator before voltage application can be calculated from value of the oxidation current measured here, and further amount of glycerol reacted with the glycerol dehydrogenase can be determined; and finally concentration of neutral fat in the sample can be calculated. Value of voltage applied in flowing oxidation current is not especially limited, and can be adjusted as appropriate with reference to conventionally known knowledge; as an example, a voltage of about −200 to 700 mV, preferably 0 to 600 mV may be applied between the reference electrode 42 and the working electrode 44. A voltage application means for applying voltage is not especially limited, and a conventionally known voltage application means may be used as appropriate.

According to the other embodiment of the present invention, a method for measuring concentration of neutral fat in a sample using the above-described biosensor 10 is provided.

As a method for measuring oxidation current value, and for converting from the current value to the substrate concentration, a chrono-amperometry method for measuring current value after a certain time from application of a predetermined voltage may be used, or a chrono-coulometry method for measuring charge amount obtained by integration of current response measured by the chrono-amperometry method with time, may be used. In view of capability of measuring by a simple apparatus system, the chrono-amperometry method can be preferably used.

Explanation was given above on examples of the embodiments for calculation of neutral fat concentration, by measurement of current in oxidizing the reductive type electron mediator (oxidation current), however, .embodiments for calculation of neutral fat concentration by measurement of current in reducing the oxidative type electron mediator left without being reduced (reduction current), may also be adopted.

EXAMPLES

Explanation will be given below specifically on the present invention, with reference to examples, however, these examples should not limit the present invention.
(Enzyme Activity)

Into a 10 mM phosphate buffer solution (pH 7) containing 0.2% of Triton X-100, which contains 50 µM DCIP, 0.2 mM PMS and 400 mM glycerol, the PQQ dependent type glycerol dehydrogenase was dissolved to prepare a solution of the PQQ dependent type glycerol dehydrogenase. A reaction between an enzyme and a substrate contained in the solution was traced by change in absorbance of DCIP at 600 nm, and the reduction rate of the absorbance was defined as reaction rate of the enzyme, and enzyme activity reducing 1 µmol of DICP in 1 minute was defined as 1 unit (U). It should be noted that molar absorbance of DCIP at a pH of 7.0 was 16.3 mM$^{-1}$.

Reference Example 1

Into a 500-mL Sakaguchi flask, 400 mL of culture media composed of sorbitol (2% by weight), yeast extract (0.3% by weight), meat extract (0.3% by weight), corn steep liquor (0.3% by weight), polypeptone (1% by weight), urea (0.1% by weight), $KH_2PO_4$ (0.1% by weight), $MgSO_4.7H_2O$ (0.02% by weight), $CaCl_2$ (0.1% by weight), with a pH of 7.0, was transferred, by 100 mL per one flask, and autoclaved at 121° C. for 20 minutes.

As an inoculum, a strain of *Gluconobacter oxydans* NBRC 3291, was inoculated by one platinum loop and cultured at 30° C. for 24 hours to make a seed culture media.

Then, 6.6 L of the culture media prepared with the same composition as in the above, was transferred to a 10-L jar fermenter, and autoclaved at 121° C. for 20 minutes, followed by gradually cooling and subsequently transferring of a 400 mL of the seed culture media, which was cultured under 750 rpm and an airflow amount of 7 L/minute, at 30° C. for 24 hours.

The culture media was subjected to centrifugal separation to collect bacterial cells, which were suspended with distilled water, and subsequently the bacterial cells were disrupted with a French press. A solution containing the disrupted bacterial cells was subjected to centrifugal separation, and the resultant supernatant was subjected to ultracentrifugal separation to yield a membrane fraction as a precipitate. This membrane fraction was suspended in a 10 mM Tris-hydrochloride buffer solution (pH 8.0), added with Triton X-100 so as to be a final concentration of 1%, and then stirred at 4° C. for 2 hours. The supernatant obtained by ultracentrifugal separation was dialyzed overnight with a 10 mM phosphate buffer solution (pH 7.0) containing 0.2% by weight of Triton X-100, and this was used as a solubilized membrane fraction. This solubilized membrane fraction was fractionated by FPLC, using Resource Q (6 mL), and the resultant activated fraction was dialyzed overnight with a 10 mM phosphate buffer solution (pH 7.0) containing 0.2% by weight of Triton X-100, and subsequently subjected to freeze-drying to yield an enzyme authentic preparation of protein with a specific activity of 3 U/mg. This glycerol dehydrogenase derived from *Gluconobacter oxydans* may simply be referred to as "GlyDH" hereinafter.

Example 1-1

As a sensor substrate formed with an electrode system, a commercial sensor electrode (manufactured by BVT Co., Ltd; AC1.W5.R1) was prepared. In this sensor substrate, the electrode system has a diameter of about 6 mm, and nearly circular shape. Furthermore, at the upper part of the electrode system prepared above, a PET sheet, with a thickness of 0.2 mm, and having a hole with a diameter of 6 mm, was glued together to form a spacer. Into the inside of the hole of the spacer on the electrode system, 10 µL of phosphate buffered saline mixed with GlyDH (20 U/mL) obtained in the above Reference Example 1, the lipoprotein lipase (manufactured by Amano Enzyme Inc., 10,000 U/mL), and 1-methoxy-5-methylphenazinium methylsulfate (manufactured by DOJINDO Laboratories, 10 mmol/L; hereinafter referred to as "m-PMS") as an electron mediator, was dropped, and dried at room temperature, to form a reaction layer.

Onto this reaction layer, 10 µL of a sample liquid containing 50 mg/dL of triolein was dropped. Triolein contained in the sample was hydrolyzed to fatty acid and glycerol by the lipoprotein lipase, and this glycerol was oxidized by GlyDH, and simultaneously the electron mediator in the reaction layer was reduced.

After 5 minutes from dropping the sample, a voltage of +150 mV was applied on the working electrode relative to the reference electrode, to measure oxidation current value of the electron mediator. In this measurement, an electrochemical measurement system HZ-SOOO (manufactured by Hokuto Denko Corp., HAG 1512 m/BP) was used. This current value (response current) is proportional to concentration of a reductant of the electron mediator, namely triolein concentration in the sample. By measurement of this current value, triolein concentration in the sample was evaluated.

It should be noted that the sample was one obtained by dissolving triolein (manufactured by Tokyo Chemical Industry Co., Ltd.) into phosphate buffered saline containing 10% by weight of Triton X-100.

Then, response current was measured similarly as in the above, except that amount of triolein contained in the sample was changed to a mg/dL, 100 mg/dL, 150 mg/dL, and 200 mg/dL. Result of plotting of current value at one second after voltage application, on samples containing each concentration of triolein, is shown in FIG. 4.

Figure 4:
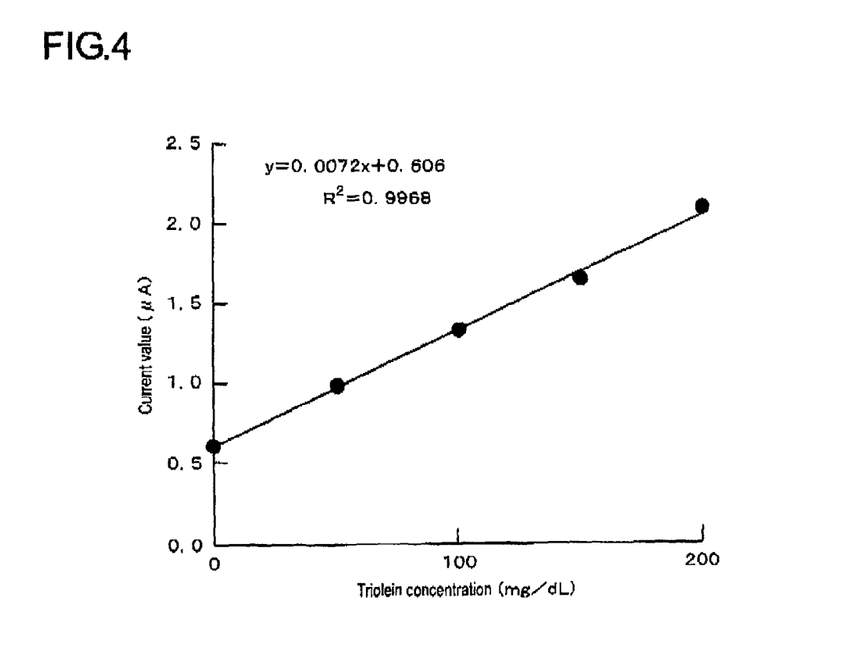
FIG. 4 is a graph showing the result of Example 1-1.

As shown in FIG. 4, good linearity was observed between response current value and triolein concentration.

Example 1-2

After dropping an aqueous solution of 0.5% (w/v) of sodium carboxymethyl cellulose (manufactured by Wako Pure Chemical Industries Ltd; hereafter may be referred to as "CMC") onto the electrode system used in Example 1-1, and drying, a 0.5% CMC solution containing GlyDH (20 U/mL) obtained in Reference Example 1, the lipoprotein lipase (10,000 u/mL) and m-PMS (10 mmol/L) was dropped, and dried to form a reaction layer.

Correlativity between response current value and triolein concentration was studied similarly as in Example 1-1, by using the biosensor. The result is shown in FIG. 5.

Figure 5:
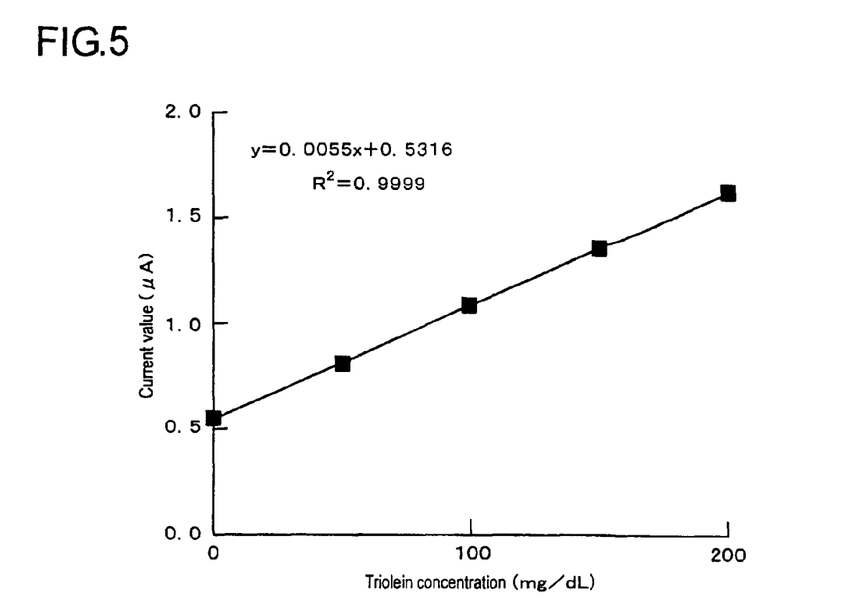
FIG. 5 is a graph showing the result of Example 1-2.

As shown in FIG. 5, although the resultant response current value was reduced a little by effect of CMC, higher correlativity between response current value and concentration of neutral fat was observed as compared with Example 1-1.

Example 2-1

As a sensor substrate formed with an electrode system, a commercial sensor electrode (manufactured by BVT Co., Ltd; AC1.WS.R1) was prepared. In this sensor substrate, the electrode system has a diameter of about 6 mm, and nearly circular shape. Furthermore, at the upper part of the electrode system prepared above, a PET sheet, with a thickness of 0.2 mm, and having a hole with a diameter of 6 mm, was glued together to form a spacer.

On the other hand, into the phosphate buffer solution (PBS) with a pH of 7.0, GlyDH (30 U/mL), as a redox enzyme obtained in the above Reference Example, the lipoprotein lipase (Amano Enzyme Inc.: 10,000 U/mL), 1-methoxy-5-methylphenazinium methylsulfate (hereafter may be referred to as "m-PMS"), as an electron mediator, (manufactured by DOJINDO Laboratories; 10 mM), carboxymethyl cellulose (CMC) (0.5% by weight) and Triton X-100 (2% by weight), as a surfactant, were added to prepare a composition for forming a reaction layer.

Into the inside of the hole having the spacer, 10 µL of the composition for forming a reaction layer prepared above was dropped, and dried at room temperature to form a reaction layer.

Furthermore, into the phosphate buffered saline with a pH of 7.0 (PBS) containing 10% by weight of Triton X-100, triolein (manufactured by Tokyo Chemical Industry Co., Ltd.) was dissolved so as to be a concentration of 100 mg/dL, to prepare a sample solution.

Onto the above reaction layer, 10 pL of a sample solution prepared was dropped. Triolein in the sample solution was hydrolyzed into fatty acid (oleic acid) and glycerol by the lipoprotein lipase, and this glycerol was oxidized by GlyDH, and simultaneously the electron mediator (m-PMS) in the reaction layer is reduced.

After 30 seconds from dropping the sample, a voltage of +150 mV was applied on the working electrode relative to the reference electrode, to measure oxidation current value of the electron mediator. In this measurement, an electrochemical measurement system HZ-5000 (manufactured by Hokuto Denko Corp., HAG 1512 m/BP) was used. This current value (response current) is proportional to concentration of the reduced type electron mediator, namely triolein concentration in the sample.

Figure 6:
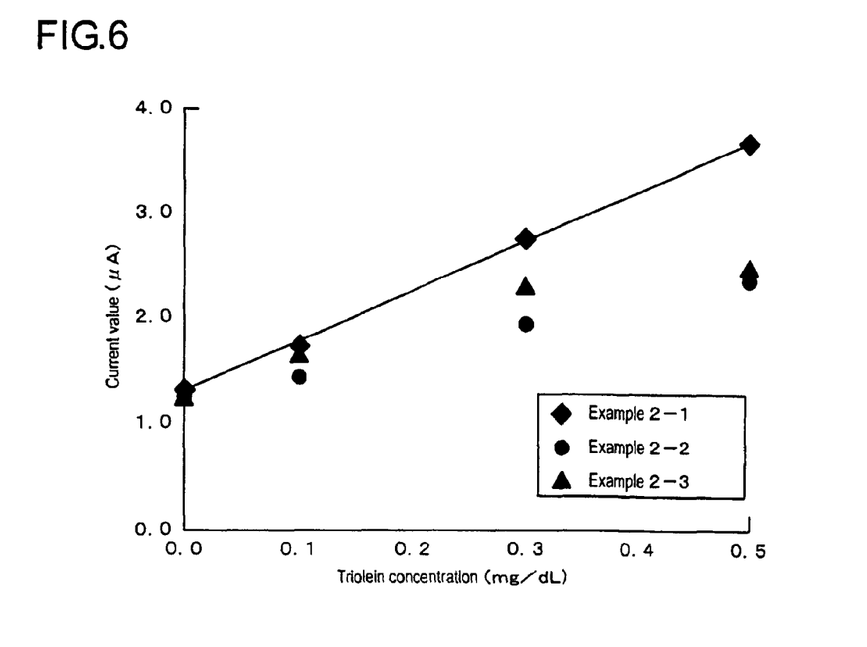
FIG. 6 is a graph showing the result of Example 2-1 to 2-3.

Then, oxidation current value was measured by a similar method as in the above, except that triolein concentration in the sample solution was changed to 300 mg/dL, and 500 mg/dL. In addition, as a control sample, a sample solution not containing triolein was prepared, and oxidation current value was similarly measured. The oxidation current value measured was plotted on a graph. This graph is shown in FIG. 6. In the graph shown in FIG. 6, larger inclination means higher measurement sensitivity of the sensor. In the present example, a graph showing relatively large inclination as shown in FIG. 6 can be obtained. Therefore, it is found that, according to the present example, a sensor excellent in measurement sensitivity is provided.

Example 2-2

A spacer and a reaction layer were formed on a sensor substrate, by a similar method as in the above Example 2-1, except that Triton X-100, as a surfactant, was not added, in preparation of the composition for forming a reaction layer, to measure oxidation current (response current) after the addition of the sample solution. A graph, wherein the results obtained were plotted, is shown in FIG. 6. In the present example, as shown in FIG. 6, a certain degree of linearity is observed, although inclination of the resultant graph is small.

Example 2-3

A spacer and a reaction layer were formed on a sensor substrate, by a similar method as in the above Example 2-1, except that distilled water was used instead of the phosphate buffered saline, in preparation of the composition for forming a reaction layer, to measure oxidation current (response current) after the addition of the sample solution. A graph, wherein the results obtained were plotted, is shown in FIG. 6. In the present example, as shown in FIG. 6, a certain degree of linearity is observed, although inclination of the resultant graph is small.

It should be noted that the present application is based on Japanese Patent Application No. 2005-095169, and Japanese Patent Application No. 2005-096427, filed on Mar. 29, 2005, whose disclosed content is incorporated herein by reference in its entirety.

The invention claimed is:

1. A biosensor for measuring concentration of neutral fat, based on value of current flowing in said electrode system, comprising:

an insulating substrate;

an electrode system having a working electrode and a counter electrode, formed onto said insulating substrate;

a reaction layer having a lipoprotein lipase, a glycerol dehydrogenase and an electron mediator, formed at the upper part or the vicinity of said electrode system; and a lead part and a connector part for making said electrode system electrically conducted to outside of the biosensor, wherein a material configuring said electrode system is a material of carbon, as a main component, with a surface resistivity value of equal to or lower than 100 $\Omega/\square$, in a thickness of 10 μm, a material configuring said lead part and said connector part is a material of metal, as a main component, with a surface resistivity value of equal to or lower than 50 $\Omega/\square$, in a thickness of 10 μm, and the glycerol dehydrogenase is pyrroloquinoline quinone dependent.

2. The biosensor according to claim 1, wherein said electrode system further comprises a reference electrode.

3. The biosensor according to claim 1, wherein said electron mediator is one kind or two or more kinds selected from the group consisting of a ferricyanide ion, p-benzoquinone and a p-benzoquinone derivative, phenazine methosulfate and a phenazine methosulfate derivative, methylene blue, thionin, indigocarmine, gallocyanin, safranin, ferrocene and a derivative thereof, α-naphthoquinone and an α-naphthoquinone derivative.

4. The biosensor according to claim 1, wherein said reaction layer further comprises a surfactant and a pH buffering agent.

5. The biosensor according to claim 4, wherein said surfactant is a nonionic surfactant.

6. The biosensor according to claim 4, wherein pH of said pH buffering agent is 6 to 9.

7. The biosensor according to claim 1, wherein said reaction layer further comprises a hydrophilic polymer.

8. The biosensor according to claim 7, wherein said hydrophilic polymer is one kind or two or more kinds selected from the group consisting of tannic acid, pectin, casein, carrageenan, furcellaran, pullulan, collagen, chitin, chitosan, sodium chondroitin sulfate, lignin sulfonic acid, and derivatives thereof.

9. The biosensor according to claim 7, wherein said reaction layer comprises:

a first reaction layer having said electron mediator and said hydrophilic polymer, but substantially not having said glycerol dehydrogenase; and a second reaction layer formed onto the upper layer of said first reaction layer, and having said glycerol dehydrogenase and said hydrophilic polymer, but substantially not having said electron mediator.

10. The biosensor according to claim 9, wherein a third reaction layer consisting essentially of said hydrophilic polymer is formed between said first reaction layer and said second reaction layer.

11. The biosensor according to claim 1, wherein an insulating layer having a nearly rectangular-shape opening part is formed at the upper layer of said electrode system, characterized in that exposure area from said opening part of said counter electrode is 1.2 to 3.0 times exposure area from said opening part of said working electrode.

12. The biosensor according to claim 1, wherein said metal is one kind or two or more kinds of metals selected from the group consisting of silver, gold, platinum and palladium.

13. The biosensor according to claim 1, wherein said glycerol dehydrogenase is a modified glycerol dehydrogenase chemically modified with a bivalent cross-linking reagent, in the presence of a surfactant.

14. The biosensor according to claim 13, wherein said glycerol dehydrogenase is derived from bacteria belonging to Gluconobacter.

15. The biosensor according to claim 2, wherein said electron mediator is one kind or two or more kinds selected from the group consisting of a ferricyanide ion, p-benzoquinone and a p-benzoquinone derivative, phenazine methosulfate and a phenazine methosulfate derivative, methylene blue, thionin, indigocarmine, gallocyanin, safranin, ferrocene and a derivative thereof, α-naphthoquinone and an α-naphthoquinone derivative.

16. The biosensor according to claim 1, wherein the reaction layer further includes carboxymethylcellulose, phosphate buffered saline, and Triton-X100, and the electron mediator is 1-methoxy-5-methylphenazinium methylsulfate.

\* \* \* \* \*